United States Patent [19]

Michel

[11] 4,251,775
[45] Feb. 17, 1981

[54] ION FLUX DENSITY PROBE

[75] Inventor: Thomas J. Michel, Hialeah, Fla.

[73] Assignee: Santek, Inc., Hollywood, Fla.

[21] Appl. No.: 16,487

[22] Filed: Mar. 1, 1979

[51] Int. Cl.³ ............................................. G01N 27/62
[52] U.S. Cl. .................................... 324/464; 324/72.5; 324/71 SN
[58] Field of Search ............ 324/72, 72.5, 459, 71 SN, 324/464

[56] References Cited

U.S. PATENT DOCUMENTS

| 3,445,757 | 5/1969 | Krucoff | 324/464 |
| 3,559,049 | 1/1971 | Liebermann | 324/464 |
| 3,864,628 | 2/1975 | Klass | 324/71 SN |

*Primary Examiner*—Michael J. Tokar
*Attorney, Agent, or Firm*—Michael Ebert

[57] ABSTRACT

A probe operable in conjunction with an electrometer having a high input impedance to provide an instrument for measuring air ion flux density. The probe structure is such that its presence in the atmosphere in which a measurement is being carried out will not give rise to perturbations in the localized electric field and therefore has no perceptible effect on the accuracy of measurement. The probe is constituted by a metal target to which the ions give up their charge, the target being supported at the end of a barrel of dielectric material by a conductor attached thereto and extending axially through the barrel to a contact at the rear of the barrel which is connected to the line of a shielded coaxial cable which couples the target to the input terminal of a grounded electrometer, the shield of the cable also being grounded. The surface of the barrel is coated with a layer of semi-conductive material that makes contact at the lower end of the barrel with the grounded cable shield. The semi-conductive layer on the barrel surrounding the target conductor therein provides a controlled leakage path extending between the target and the grounded cable shield that approximates the characteristics of the atmosphere and the input impedance of the electrometer whereby the presence of the probe in the atmosphere introduces substantially no discontinuity in the localized electric field.

11 Claims, 6 Drawing Figures

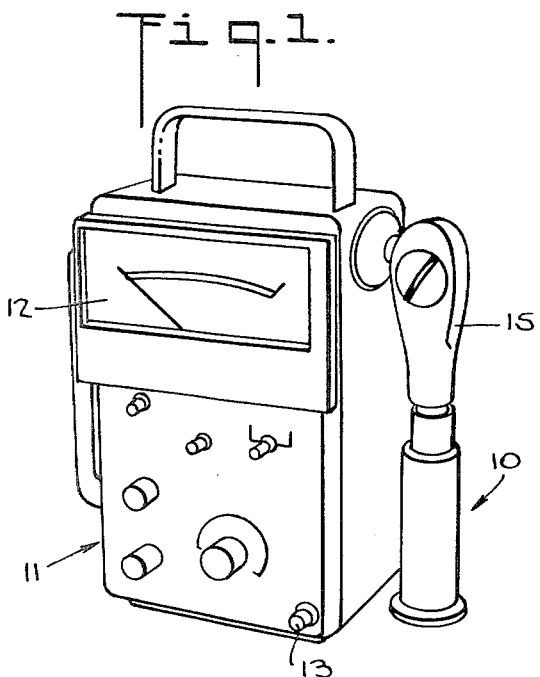
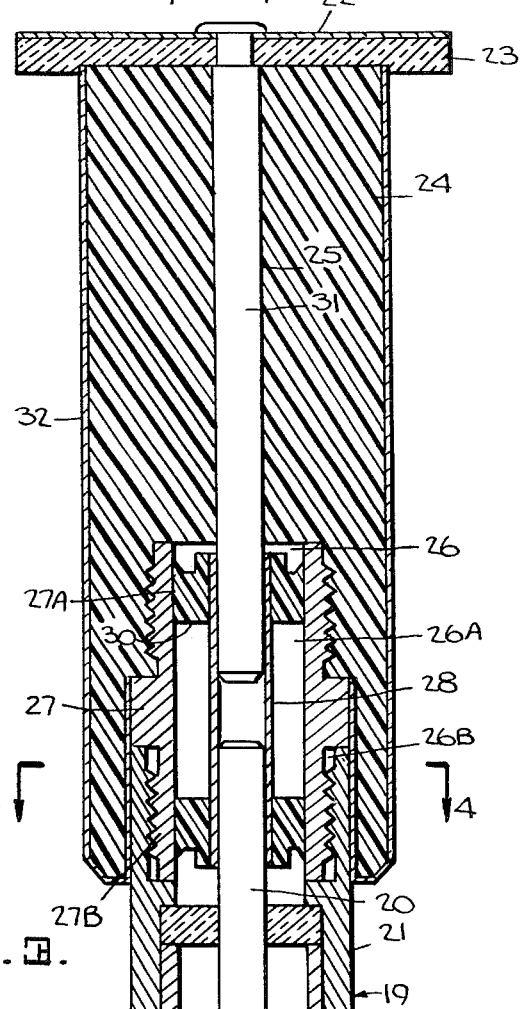
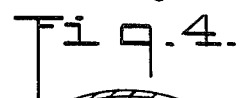
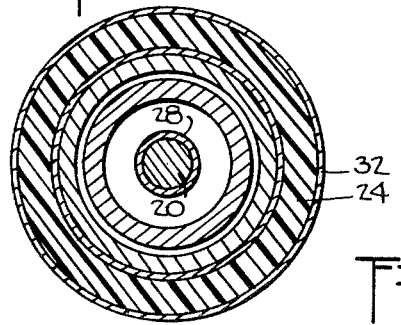
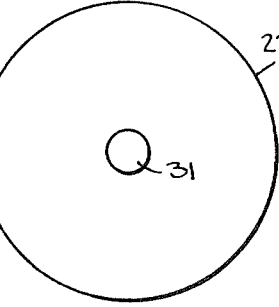
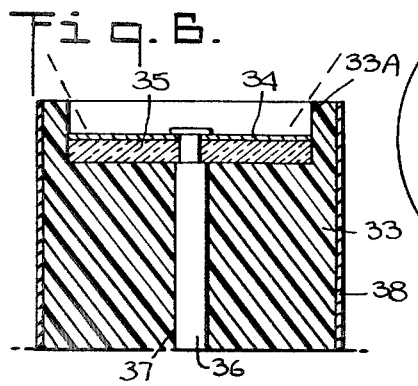
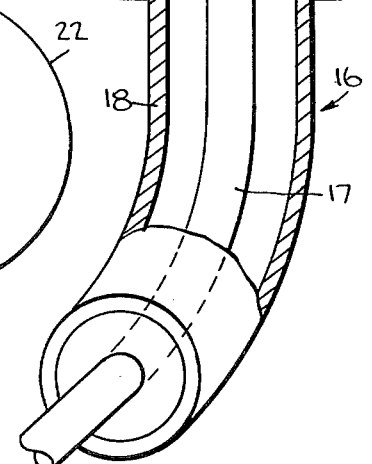
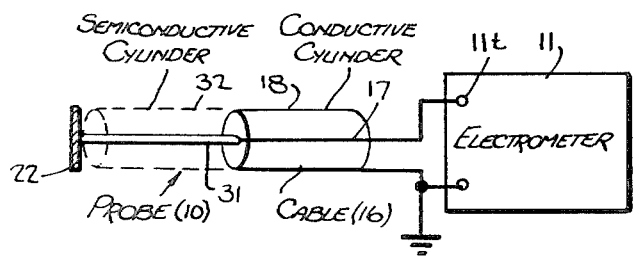

ION FLUX DENSITY PROBE

BACKGROUND OF THE INVENTION

1. Field of the Invention

This invention relates generally to instruments for the measurements of gas ion flux density, and more particularly to a probe for this purpose whose presence in the atmosphere in which a measurement is being made does not give rise to perturbations in the localized electric field and therefore has no appreciable effect on the accuracy of measurement.

2. Prior Art

In a gas such as air, ionization takes place as a result of an electric discharge through the gas which dislodges electrons from neutral gaseous atoms so that the atoms then become charged ions. Each gas has a critical voltage at which the ionization phenomenon is initiated.

A corona discharge is a highly active glow region in the atmosphere surrounding a discharge electrode. If this electrode is constituted by a wire, the glow region extends a short distance beyond the wire. Assuming that the wire is negatively charged, the free electrons in the gas in the region of the intense electric field surrounding the wire gain energy from this field to produce positive ions and other electrons by collision. In turn, these new electrons are accelerated and produce further ionization.

This cumulative process results in an electron avalanche in which the positive ions are accelerated toward and bombard the negatively-charged wire. As a consequence of such ionic bombardment, secondary electrons are ejected from the wire surface which act to maintain the discharge. Moreover high-frequency radiation originating from excited gas molecules lying within the corona region contribute to the supply of secondary electrons.

The electrons emitted from the negatively-charged wire or discharge electrode are drawn toward a positively-charged electrode. As these electrons advance into the weaker field away from the wire, they tend to form negative ions by attaching themselves to neutral oxygen molecules. These negative ions create a dense unipolar cloud that occupies most of the gap between the electrodes and constitutes the only current in the entire space outside of the corona glow region. This space charge functions to retard the further emission of negative charge from the corona region and in this way restricts the ionizing field adjacent the wire, thereby stabilizing the discharge.

The type of corona produced depends on the polarity of the discharge or ionizing electrode. In the example given above, we have assumed a negative polarity, in which case positive ions are accelerated toward the electrode and negatively-charged oxygen ions are repelled therefrom to produce a corona discharge. Conversely, when the polarity of the ionizing electrode is positive, negative ions are accelerated toward the electrode, causing the breakdown of air molecules with the result that positive ions are repelled outward from the ionizing electrode to create a corona glow.

The measurement of gaseous ions using the flux density technique has many useful practical applications. Ion flux density instruments may be used to measure the output of ionizing sources, to measure atmospheric ion flux as well as to monitor ion activity in research and development projects. Thus in searching for defects in high voltage electrical components and assemblies, ultra low current leakage can readily be detected by probing the atmosphere surrounding the items being tested for ion activity, even before the onset of corona, in order to determine the location of the ion source.

The probe conventionally used for this purpose includes a metal target of known area, the number of ions that give up their charge to this target being indicated in terms of an electrical current induced in an electrometer connected to the target. Because the target has a known area, the amount of current it receives affords an index to the ion flux density.

An electrometer is a highly sensitive instrument which is capable of measuring low-level potentials in that it has an extremely high input impedance. Before the introduction of electronic electrometers of the vacuum tube and later of the solid-state type, electrometer measurements were generally carried out by moving-coil galvanometers. For example, the solid-state ion flux meter (model 700) marketed by Santek, Inc. of Hollywood, Florida, has an extremely high input impedance and is capable of measuring currents of the order of $1 \times 10^{-14}$ amperes.

In existing types of probes associated with electrometers, the metal target is generally disc-shaped and is mounted at one end of a supporting barrel fabricated of dielectric material, the target being connected to a conductor extending axially through the barrel and joined to the inner tubular connector of a jack socketed in the other end of the barrel. Connection to the input terminal of the electrometer is effected by a shielded cable whose end coupler has a plug which is inserted in the inner connector of the jack and a ring which is joined to the outer connector. The electrometer and the shield are both grounded.

The presence of a probe of this type in an atmosphere whose ion flux density is to be measured gives rise to localized electric field perturbations which introduce an error in the reading so that the instrument is lacking in accuracy. The reason for this inaccuracy will now be explained.

Air ions flow along electric field lines of force, these force lines being lines of potential difference. When a probe connected to an electrometer is placed in an atmosphere having ions therein, the probe is usually the component of lowest resistance in the circuit, for the electrometer presents an extremely high impedance to the ion source and so does the atmosphere.

The barrel of the probe is of dielectric material, and in the presence of an electrostatic field a boundary surface charge quickly builds up on the surface of the barrel which interfaces with the atmosphere. This surface charge reduces the electric field gradient between the probe and the source to a value approaching zero. When this condition is brought about, few ions will strike the target. As noted previously, air ions flow along electric lines of force created by a potential difference; and when this difference is close to zero, there is little ion flow.

This drawback cannot be overcome by making the barrel of the probe of a conductive material, for then the barrel will present a ground plane to the atmosphere. This ground plane is artificial, for it increases the voltage gradient and brings about a higher flow of ions than would occur were the probe's grounding effect removed. Hence with a conductive barrel in a flux density probe, the reading would be inaccurate.

SUMMARY OF INVENTION

In view of the foregoing, the main object of this invention is to produce a probe for a gas ion flux density-measuring instrument whose presence in the atmosphere produces no perturbations in the localized electric field whereby the reading of the instrument is undisturbed and highly accurate.

More particularly, an object of this invention is to provide a probe of the above type having a target supported at the upper end of a barrel of dielectric material whose surface is coated with a layer of semi-conductive material that makes contact at the lower end of the barrel to the grounded shield of a cable connecting the target conductor to the input terminal of the electrometer.

A significant feature of a probe in accordance with the invention is that the semi-conductive layer on the barrel produces a controlled current leakage path along the barrel surface that closely approximates the characteristics of the atmosphere and of the input impedance of the electrometer so that the barrel presence in the atmosphere introduces no disturbance in the localized electric field.

Also an object of the invention is to provide a probe of the above type having directional characteristics, making it possible, when measuring ion flux density, to determine the precise point of origin of the gas ion stream.

Briefly stated, in a probe in accordance with the invention, a metal target is supported at the upper end of a barrel of dielectric material by means of a conductor attached to the target and extending through an axial bore in the barrel to join the inner connector of a jack socketed in the barrel at the other end thereof, the jack having a cylindrical outer connector concentric with the inner connector.

The probe is linked to the input of an electrometer by a shielded cable terminating in a coupler having a plug which is insertable in the inner connector of the jack, the plug being coaxial with a ring that is joined to the outer connector of the jack. The coupler ring is connected to the cable shield and lies in physical contact with the surface of the barrel. The shield and the electrometer are both grounded.

The surface of the barrel is coated with a layer of semi-conductive material which at the lower end of the barrel is in electrical contact with the ring. This layer produces a controlled leakage path that closely approximates the characteristics of the atmosphere and of the input impedance of the electrometer whereby the presence of the probe in the atmosphere introduces no discontinuity in the localized electric field.

OUTLINE OF DRAWINGS

For a better understanding of the invention as well as other objects and further features thereof, reference is made to the following detailed description to be read in conjunction with the accompanying drawings, wherein:

FIG. 1 is a perspective view of an ion air flux density meter which includes one preferred embodiment of a probe in accordance with the invention;

FIG. 2 is a longitudinal section taken through the structure of the probe;

FIG. 3 is a top plan view of the probe;

FIG. 4 is a transverse section taken on the plane indicated by line 4—4 in FIG. 2;

FIG. 5 schematically illustrates the conductive and semi-conductive regions of the probe structure; and FIG. 6 is a section taken through the upper portion of another embodiment of a probe in accordance with the invention, the probe having directional characteristics.

DESCRIPTION OF THE INVENTION

Ion Flux Density Measuring Instrument

Referring now to FIG. 1, there is shown an ion-flux instrument capable of accurately measuring minute currents generated when gas ions strike the target of a probe 10 included in the instrument. The probe is coupled to a solid-state electrometer 11 provided with an ion flux current indicator 12, the electrometer being grounded by a cable plugged into a ground jacket 13. This instrument, in the form shown, is battery-operated and portable, and is capable of measuring positive and negative ion flux, a polarity reversing switch 14 being provided for this purpose.

The electrometer circuit is of the type included in the above-identified Model 700 ION FLUX METER and sold by SANTEK, Inc. Since the circuit of this commercially-available electrometer forms no part of the present invention, its details will not be further described except to note the following specifications:

Resolution: $1 \times 10^{-14}$ amps.
Range: $\pm 1 \times 10^{-4}$ to $1 \times 10^{-13}$ amps.
Frequency Response: DC to 5 Hz.
Input resistance: $> 1 \times 10^{10}$ ohms.

Probe 10 is supported on an arm 15 that swivels through 180° and can be removed to expand its flexibility by attaching a shielded extension signal cable thereto. Thus any distance from an ion source, the meter allows flux measurement to be made. In the meter shown in FIG. 1, the cable which couples probe 10 to electrometer 11 is incorporated in a swivel arm 15; whereas in the arrangement shown in FIG. 2, an extended coaxial cable 16 is provided for this purpose.

The instrument may be used to verify output from an ionized source as well as to measure the ion diffusion from a source. The meter can also function as a standard output measure, in which case probe 10 is placed exactly 10 cm. from the ion source and a reading taken. This reading, expressed in A.K.U., is fixed to 10 cm. to reduce the effects of any air movement on the electric field which might influence the reading at a greater distance.

An A.K.U. or an Alber Krueger Unit, is a unit of measure of air ion flux (of ions smaller than 35 millimicrons in diameter) from an ion source. One A.K.U. unit of negative air ion flux is equivalent to 1 nanoampere per square cm. of ion current measured at 10 cm. from the source at S.T.P. with 35 to 45% R.H. While A.K.U. is usually used to quantify negatively-charged ions, it may also be used to quantify positively-charged ions by the use of the notation A.K.U.+.

Inasmuch as this unit of measure is original with applicant, the conditions under which this metrological unit are established will now be set forth.

A. The target disc of the probe is made of 0.015 inch oxygen-free hard copper laminated to G-10 epoxy glass, $\frac{1}{8}$ inch thick. This disc has a 10 sq. cm. area $\pm 0.1$ mm sq., with its conductor protruding from the back or glass side so as not to impede the ion flow toward the face of the disc.

B. The disc conductor is connected to the input terminal of a femmto-ammeter by a two-meter length RG 59/U coaxial transmission line, the shield of the line and the femmto-ammeter being well-grounded.

C. The dead air atmosphere in which the measurement is taken is at standard temperature and pressure (S.T.P.) and between 35 and 45 percent relative humidity. For this purpose, analytic air is preferably used so that it is free of pollutants.

D. The target disc is placed in an unobstructed path in front of the output head of an ion generator parallel to the plane surface of the head, this relationship being maintained by a suitable mechanical clamp. When the ion generator has a needle type discharge electrode, the target disc in this instance is placed in a plane normal to the axis of the needle 10 cm. from the point thereof.

E. The device under test is placed so that no interfering objects appear within a spherical radius of 1.5 meters; i.e., by placing the device on a pedestal in the center of a shielded test chamber.

The concern of the present invention is with the structure and functional characteristics of probe 10. This probe is designed so that its physical presence in the atmosphere in which a measurement is being carried out will not give rise to measurable perturbations in the localized electric field and therefore will have no appreciable effect on the accuracy of measurement.

The Probe (First Embodiment)

Referring now to FIGS. 2, 3 and 4, there is shown a probe, generally designated by numeral 10, which is coupled to electrometer 11 through coaxial cable 16 whose inner line 17 is connected to the input terminal $11_t$ of the grounded electrometer 11 and whose outer shield 18 which surrounds the inner line and is insulated therefrom as grounded through the grounded electrometer.

Shielded cable 10 extending between electrometer 11 and probe 10 is terminated by a coupler 19 constituted by an inner plug 20 and a ring 21 concentric therewith. Probe 10 includes a disc-shaped metal target 22 of high electrical conductivity which is laminated to a dimensionally-stable insulating base 23, whose undersurface has a shallow circular well formed therein to nest the upper end of a barrel 24 of dielectric material. Barrel 24 is provided with a small diameter axial bore 25. Bore 25 extends between the upper end of the barrel and a circular bore 26 of larger diameter formed in the lower end portion of the barrel.

The upper end portion 26A of bore 26 is internally threaded for engagement by the internally-threaded upper end section 27A of the cylindrical outer connector 27 of a jack socketed in bore 26. The lower end section 27B of outer connector 27 lies within the lower end portion 26B of bore 26. The diameter of bore 26 is enlarged to provide an annular space to accommodate ring 21 of coupler 19. This ring is threadably received on end section 27B of the jack outer connector.

The probe jack further includes a tubular inner connector 28 which is coaxially supported within outer connector 27 by spaced insulating washers 29 and 30. Plug 20 of the cable coupler is insertable in the lower end of the tubular inner connector 28 of the jack. Target 22 is welded or otherwise attached at its center to a rod-shaped conductor 31 which extends through axial bore 25 in the barrel, the end of the conductor being inserted into the upper end of inner connector 28, thereby connecting target 22 to the input terminal $11_t$ of the electrometer in a series path defined by target conductor 31, inner connector 28 of the jack, plug 20 of the cable coupler and the inner line 17 of shielded cable 16.

It is important for purposes of air ion flux measurement that a high insulation factor be maintained about the current-carrying member of the probe which in this instance is rod-shaped conductor 31. To this end, barrel 24 is fabricated of a dielectric material having extremely good insulating characteristics as well as high structural strength, such as a polycarbonate or a molded acrylic material.

As pointed out previously, if the dielectric surface of barrel 24 were directly exposed to the atmosphere, the electrostatic charge build-up thereon would reduce the electric field gradient to a value so low that few air ions would strike the target; whereas if the surface of the barrel were conductive in nature, it would then raise the electric field gradient and give rise to an excessive flow of ions. In either case, the resultant current flow would not be an accurate index to the prevailing ion flux density.

To overcome this drawback, the surface of barrel 24 is coated, preferably using a spray or dip technique for this purpose, with a flowable compound or paint having semi-conductive characteristics to produce, when cured, a solid semi-conductive layer 32 which covers the entire outer surface of barrel 24 and extends into the lower end section 26B of bore 26 to coat the surface thereof and to make physical and electrical contact with ring 21 of the cable coupler.

Ring 21 is connected to cable shield 18 which is grounded. In practice, semi-conductive layer 32 may be formed by a carbon or metal dispersion in a liquid acrylic solution of other insulating matrix which has an affinity for the barrel material and, when cured, strongly adheres thereto. This layer creates a leakage path extending between the target and ground.

Thus, as illustrated in FIG. 5, target 22 is connected by its conductor 31 and by the inner line 17 of cable 16 to input terminal 11t of electrometer 11 which is grounded through its panel jack 13, the cable shield 18 also being grounded thereby.

In operation, semi-conductive layer 32 on the surface of the probe barrel acts as a controlled current leakage path extending between the target 22 and the grounded shield 18 of cable 16. The semi-conductive layer is formulated so as to provide a leakage path whose characteristics closely approach those of the atmosphere and of the high input impedance of the electrometer. In this way, the probe has no appreciable effect on the localized electric field in which it is present and neither provides a surface on which a charge can build up nor an artificial ground.

At the same time, target conductor 25 which conducts the current reflecting the ion flux density is surrounded by highly insulating barrel material that isolates it from the surface of the barrel. The inner line 17 of the coaxial cable is similarly isolated from the grounded shield 18, thereby insuring both measurement accuracy and operator safety.

It is to be understood that the probe geometry shown in FIGS. 2, 3 and 4 is by way of illustration only, and that in practice the invention is applicable to any useful probe shape, such as a probe whose barrel has a tapered form so that the tip thereof has a very small diameter for supporting a small target of similar diameter. And while in the above description, probe 10 is coupled to a solid-state electrometer, in practice any sensitive current-responsive indicator having a high input impedance may be used for this purpose.

Directional Probe (Second Embodiment)

When measuring air ion flux, it is sometimes desirable to be able to determine the precise point of origin of the ion stream. When using known forms of probes having a conductive target, this maneuver is difficult to carry out because of the $4\pi$ steradian sensitivity of the probe. When, for example, a printed circuit board assembly is being probed for faults by determining which areas are going into corona because of an insulation defect and which areas are corona free, a directional probe is then desirable.

To this end, as shown in FIG. 6, the insulating barrel 33 of the probe is provided at its upper end with a circular recess 33A within which is nested a disc-shaped target 34 laminated to a disc-shaped insulating base 35 which rests on the floor of the recess. This target is attached at its center to a conductor 36 which extends through an axial bore 37 in the barrel. The surface of barrel 33 is coated with a semi-conductive layer 38.

In all other respects, save for the recessed target, the probe structure is essentially the same as that shown in FIGS. 1 and 2. Thus the circular edge of the target is surrounded by a semi-conductive cylindrical ion-shield and only the face of the target which lies below the rim of the ion-shield is exposed to an ion stream.

The reason this probe is directional is that the recess 33A functions as a sensitivity window which acts to define the angular limits of the receptivity range of the target to an incoming ion stream. The deeper the recess, the narrower is the angular range. In practice, it is possible to control the sensitivity window from approximately a 5° steradian minimum to a 180° steradian maximum, the latter value being obtained in the absence of a recess. By varying the conductivity of the semiconductive layer 38 and the depth of the recess, one is able to adjust precisely the probe's directional response characteristics to satisfy predetermined requirements.

While there have been shown and described preferred embodiments of an ion flux density probe in accordance with the invention, it will be appreciated that many changes and modifications may be made therein without, however, departing from the essential spirit thereof.

I claim:

1. An instrument for measuring gas ion flux density constituted by a probe placeable in the atmosphere to be tested and coupled by a coaxial cable having an inner line and an outer shield to the input terminal of a current-indicating device having a high input impedance, said shield and said device being grounded, said probe comprising:

A. a conductive target, to which ions give up their charge, supported at one end of a barrel formed of dielectric material, said target being connected by a conductor passing through said barrel to a terminal at the other end of the barrel making electrical contact with the inner line of said cable; and B. a semi-conductive layer coated on the surface of said barrel and extending to the lower end thereof to effect a connection with the shield of said grounded cable, said layer providing a controlled leakage path extending between the target and the shield that approximates the characteristics of the atmosphere and the input impedance of the device, whereby the presence of the probe in the atmosphere gives rise to no perturbations in the localized electric field and therefore has no perceptible effect on the accuracy of measurement.

2. An instrument as set forth in claim 1, wherein said target is laminated to an insulating base which rests on the one end of the barrel.

3. An instrument as set forth in claim 1, in which said target is formed of a copper-based metal.

4. An instrument as set forth in claim 1, wherein said semi-conductive layer is formed by a dispersion of conductive particles in an electrically insulating matrix.

5. An instrument as set forth in claim 4, wherein said matrix is of material compatible with the barrel material.

6. An instrument as set forth in claim 5, wherein said barrel material is an acrylic.

7. An instrument as set forth in claim 1, wherein said target conductor is joined to the inner tubular connector of a jack socketed in a bore in the other end of the barrel, said jack having a cylindrical outer connector whose diameter is such that an annular space is formed between the lower end thereof and the wall of the bore, said cable terminating in a coupler having a plug connected to the inner line and inserted in the inner connector of the jack and having a concentric ring which is inserted in said space and joined to the outer connector of the jack, said ring being connected to said shield and making physical contact with said semi-conductive layer.

8. An instrument as set forth in claim 1, wherein said device is an electrometer.

9. An instrument as set forth in claim 8, wherein said electrometer has a polarity-reversing switch which renders said electrometer selectively responsive to negative or positive ions.

10. An instrument as set forth in claim 8, wherein said electrometer has an ion-flux density indicator.

11. An instrument as set forth in claim 1, wherein said target is recessed within said one end of the barrel and its edge is surrounded and shielded by said semi-conductive layer, whereby said probe has directional characteristics determined by the depth of the recess.

* * * * *